United States Patent [19]

Weigert

[11] 4,064,171

[45] Dec. 20, 1977

[54] PROCESS FOR PREPARATION OF AROMATIC AMINES

[75] Inventor: Frank Julian Weigert, Wilmington, Del.

[73] Assignee: E. I. Du Pont de Nemours and Company, Wilmington, Del.

[21] Appl. No.: 694,554

[22] Filed: June 9, 1976

Related U.S. Application Data

[63] Continuation-in-part of Ser. No. 611,914, Sept. 10, 1975, abandoned, which is a continuation-in-part of Ser. No. 488,825, July 15, 1974, abandoned.

[51] Int. Cl.$^2$ .............................................. C07C 85/02
[52] U.S. Cl. ..................................................... 260/581
[58] Field of Search ......................................... 260/581

[56] References Cited

U.S. PATENT DOCUMENTS

| 2,450,640 | 10/1948 | Denton et al. | 260/581 X |
| 2,980,735 | 4/1961 | Bloch | 260/578 |
| 3,231,616 | 1/1966 | Jones | 260/581 |
| 3,553,268 | 1/1971 | Solomon et al. | 260/581 |
| 3,919,155 | 11/1975 | Squire | 260/581 X |
| 3,931,298 | 1/1976 | Wollensak | 260/581 |
| 4,001,260 | 1/1977 | Del Pesco | 260/581 X |

FOREIGN PATENT DOCUMENTS

| 815,064 | 6/1969 | Canada | 260/581 |
| 453,546 | 12/1948 | Canada | 260/581 |
| 1,327,493 | 8/1973 | United Kingdom. | |

OTHER PUBLICATIONS

Dadashev, CA 81:3397t (1974).
Dadashev et al., CA 69:99832g (1968).

Primary Examiner—Daniel E. Wyman
Assistant Examiner—Thomas A. Waltz
Attorney, Agent, or Firm—Anthony P. Mentis

[57] ABSTRACT

In the catalytic reaction of cyclohexane or an alkylated cyclohexane with ammonia to produce aniline or an alkylated aniline, the presence of water is beneficial in increasing the amount of aromatic amines produced, or in reducing the amount of undesired by-products, or both. The amount of water is 1 to 70 mole percent based on the total amount of the cyclohexane reactant and water used. The catalysts used are exemplified by zinc oxide, titanium oxide, etc.; metal compounds such as vanadates, molybdates and titanates; and cadmium sulfide, zinc selenide and the like.

36 Claims, No Drawings

PROCESS FOR PREPARATION OF AROMATIC AMINES

CROSS-REFERENCE TO RELATED APPLICATIONS

This application is a continuation-in-part of application Ser. No. 611,914 filed Sept. 10, 1975 now abandoned which in turn is a continuation-in-part of application Ser. No. 488,825 filed July 15, 1974, now abandoned.

BACKGROUND OF THE INVENTION

1. Field of the Invention

Aniline and alkyl anilines are obtained by the reaction of anhydrous ammonia with cyclohexane or cyclohexane having up to two lower alkyl substituents at elevated temperatures, such as 300°–650° C, in the presence of selected catalysts, such as zinc oxide alone or with vanadium, molybdenum or titanium oxides, etc.; metal compounds such as vanadates, molybdates and titanates; and cadmium sulfide, zinc selenide and the like. The presence of water in this reaction is beneficial in increasing the amount of aniline produced, or in reducing the amount of undesired by-products, or both.

2. Prior Art

Aniline has been prepared heretofore by reduction of nitrobenzene or by ammonolysis of chlorobenzene. Other methods of producing aniline are also known. For example, a noncatalytic method reacts cyclohexane, ammonia and sulfur, as shown in Canadian Pat. No. 815,064.

A catalytic method is shown in Bloch, U.S. Pat. No. 2,980,735 where an alkylcyclopentene is heated in the presence of cobalt metal or nickel metal. Oxides of metals of Group V, VI and VII are disclosed as possible components of the catalyst.

Another method is that shown in British patent 1,327,493 which discloses the heating of an aromatic compound such as benzene with ammonia in the presence of water and a nickel/nickel oxide catalyst.

In pending application U.S. Ser. No. 687,175 filed May 17, 1976, a continuation-in-part of U.S. Ser. No. 536,584, filed Dec. 26, 1974, now abandoned, which was a continuation-in-part of U.S. Ser. No. 445,914, filed Feb. 26, 1974, now abandoned, there is disclosed the reaction of catalytically reacting cyclohexane and ammonia to produce aniline, but in the absence of water. It has now been found that when this reaction is carried out in the presence of a designated amount of water, benefits are obtained, as for example, increasing the amount of aniline produced, or reducing the amount of undesired by-products, or both.

DESCRIPTION OF THE INVENTION

The invention is the process which consists essentially in heating a cyclic aliphatic hydrocarbon of the formula

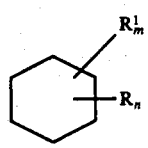

with ammonia at 300°–650° C. to produce a compound of the formula

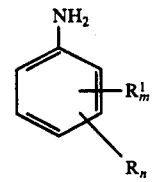

wherein
R and $R^1$ individually are alkyl of 1–4 carbon atoms and
$m$ and $n$ individually are 0 or 1,
where the heating is carried out in the presence of about 1 to about 70 mole percent of water based on the total amount of water and the said cyclic aliphatic hydrocarbon at a contact time of about 0.1 second to about 10 minutes, and in the presence of a catalyst selected from:

A. one or more oxides of Al, Cd, Ce, Fe, In, Sn, Ti, Th, Zn and Zr;
B. vanadium oxide and one or more oxides of Ag, As, Ba, Ca, Cd, Ce, Co, Cu, Eu, Fe, Gd, Hf, In, La, Mg, Mn, Ni, P, Pb, Sb, Sn, Sr, Ti, U and Zn;
C. titanium oxide and one or more oxides of Bi, Cr, Cu, Mo, Pb, U and W;
D. zinc oxide and one or more oxides of Cr, La, Mg, P, Si, Sb, W and the pair of Bi and Mo;
E. aluminum oxide, and one or more oxides of Cu, Eu, La, Mn, Pb and U;
F. aluminum oxide, molybdenum oxide and one or more oxides of Ca, Cd, Ce, Cu, Er, Fe, In, La, Ni, Pb, Sm, Sr, Ti, U, Y and Zn;
G. aluminum oxide, tungsten oxide and one or more oxides of Ca, Ce, Cu, Fe, In, La, Pb, Sm, Ti, U and Zn;
H. aluminum oxide, titanium oxide and one or more oxides of Cr, Mg, Te and V;
I. aluminum oxide, titanium oxide, zinc oxide and one or more oxides of Ag, Bi, Ca, Co, Cr, Cu, Hg, Mg, Nb, Ni, Pb, Pr, Ru, Sm, Sr, V, Yb and Y;
J. aluminum oxide, molybdenum oxide, bismuth oxide and one or more oxides of Ca, Cu, Pb, Ti and Zn;
K. aluminum oxide, molybdenum oxide, zirconium oxide and one or more oxides of Ce, Ti and Zn;
L. molybdenum oxide and one or more oxides of Cd, Ce, Cu, Fe, Gd, La, Mg, Mn, Nb, P, Pb, Ti and Zn;
M. zinc oxide, titanium oxide and one or more oxides of Cr, La, Mg and Nb;
N. CdS; CoS; CdS/aluminum oxide, CdS/titanium oxide/aluminum oxide; chromium sulfide; ZnSe; ZnS; ZnTe; ZnS/aluminum oxide; CdS/ZnS/aluminum oxide; and $WS_2$;
O. aluminum oxide, vanadium oxide and one or more oxides of Ag, Ba, Ca, Cd, Cu, Ga, In, La, Mg, Pb, Sr, Y, Zn and Zr; and
P. zinc oxide, titanium oxide, lanthanum oxide and one or more oxides of Al, Cd, Ce, Th and Zr.

The reaction may be depicted as

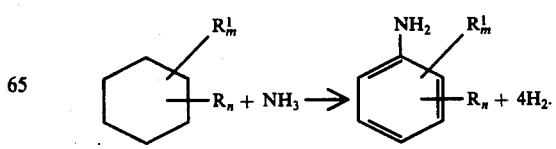

The term "oxide" includes binary oxides, ternary oxides, quaternary oxides and higher polynary oxides as well as solid solutions and non-stoichimetric oxides. It includes a single oxide; mixed oxides of a single metal in different valence states such as FeO and $Fe_2O_3$, etc.; and mixed oxides of different metals such as physical mixtures of zinc oxide and aluminum oxide, etc. and also oxides such as $Zn_3V_2O_8$, $Bi_4ZnMo_3O_{16}$, $CdSnO_3$ and the like. The invention is a broad one in that any and all combinations of the metal oxides, as set forth in the groups above, are operative catalysts. The metal oxides may be used in all proportions. It is advantageous that a member of Group A or vanadium oxide comprise half or more of a multicomponent catalyst.

Preferred for their ability to convert cyclohexane to aniline are catalysts containing zinc oxide/titanium oxide and catalysts containing zinc oxide/vanadium oxide. In each of these instances one or more other metal oxides of the invention can be present.

Preferred for their stability in the catalyst reactivation process (see below) are zinc oxide/titanium oxide/lanthanum oxide; zinc oxide/titanium oxide/zirconium oxide; and zinc oxide/titanium oxide/thorium oxide.

The amount of water in the reaction is expressed as mole percent of the total amount of water and the cyclic aliphatic hydrocarbon, i.e. cyclohexane, and ranges from about 1 to about 70 mole percent. A preferred range is about 3 to about 32 mole percent. Amounts higher than about 70 mole percent may be used but no particular advantage results therefrom.

In addition to cyclohexane, alkyl cyclohexanes having up to 2 alkyl groups having no more than 4 carbons in each alkyl can be used. These include methylcyclohexane, ethylcyclohexane, propylcyclohexane, n-butylcyclohexane, 1,2-dimethylcyclohexane, 1,4-dimethylcyclohexane, 1,3-di-n-butylcyclohexane and 1,4 diethylcyclohexane, which yield anilines such as aniline, methylaniline, ethylaniline, propylaniline, n-butylaniline and the various dimethylanilines, diethylanilines and dibutylanilines.

Temperatures in the range of 300°–650° C. are employed, but the specific optimum temperature is dependent upon the particular catalyst used and on other conditions such as pressure, contact time, and ratio of reactants. Preferred, however, is the range of 400°–600° C; more preferred is the range of 450°–550° which generally gives the highest yields and conversions.

The molar ratio of the cyclic hydrocarbon to ammonia can vary from 1/100 to 10/1. A preferred range is 5/1 to 1/10.

Elevated pressures up to more than 500 atmospheres can be used in carrying out the reaction but pressures in the range of 0.5 to 20 atmospheres are presently preferred.

The aromatic amine is produced when the reactants make physical contact with the catalyst at the reaction temperature. Accordingly any amount of catalyst can be used since it merely needs to be present in order for the reaction to occur and may be simply designated as a catalytically effective amount. The time during which the reactants are in contact with the catalyst at the reaction temperature is the contact time and can vary over a wide range. For economic operation it can range from about 0.1 second to about 10 minutes. A preferred range is about 1 second to about 8 minutes.

It is preferred to operate in a nonoxidative atmosphere, i.e. one in which molecular oxygen or similar oxidizing gases are absent. Generally this results in fewer undesired by-products. However, the reaction can be carried out with as much as 0.5 mole, but preferably no more than 0.2 mole, of molecular oxygen being present per mole of the cyclic aliphatic starting hydrocarbon. The process can be carried out in an inert atmosphere of nitrogen, helium, argon, neon and the like. A convenient method by which the oxygen may be excluded from the system is to pass steam and/or hydrocarbon continuously through a reactor containing the catalyst to flush out the air prior to heating the reactants to start the reaction.

Operating in the presence of a small amount of air can have the advantage of lessening the formation of carbon deposits on the catalyst but has the disadvantage of increasing the amount of undesired by-products.

Combinations of two or more catalysts are especially useful in providing desired activity, selectivity, long life, and the like. Relatively inert catalyst carriers or diluents can be present, e.g., carbon, silicon carbide, silica, magnesia, boron phosphate, and the like, as known in the art.

The catalysts can be made by any conventional or suitable method known in the art. For example, these methods include direct heating of the elements in air to form the oxides. Other methods include evaporation, impregnation or precipitation, each followed by calcination.

In the precipitation method, aqueous solutions of the desired constituents are mixed with a solution of a precipitating agent. A variety of bases or base forming compounds can be used as precipitating agents as for example aqueous ammonia, ammonium carbonate, ammonium bicarbonate, urea and the like. The presence of impurities in the final catalyst is minimized by carrying out the precipitation with dilute solutions and by using ammonia or ammonia salts as the precipitant along with nitrates of the desired metals. The resulting precipitate then requires a minimum of washing since any absorbed material remaining can be removed in the subsequent calcination step. The use of nitrates is recommended since other anions such as sulfate or halide generally act as catalyst poisons. Where a metal halide or sulfate is used, it is important to wash the precipitated material thoroughly to remove such deleterious ions.

In the impregnation method, a solution of an active component or components is contacted with a support to thoroughly wet it. An excess of the impregnating solution is generally used and when the support is thoroughly saturated, the excess solution is removed, as by filtration or decantation. The impregnated support is then dried and subjected to calcination. The use of nitrate solutions is also recommended in this method.

In the evaporation method, the desired components are mixed together with water to form a slurry or solution. The water is evaporated and the resultant solid is then dried and calcined. This method is of value where unwanted materials are not present and a washing step is not needed.

In the calcination step which decomposes the salts such as the carbonates or nitrates to the oxides, the catalyst material is heated in air to a temperature which is generally below 800° C. The calcination is usually carried out for a period of hours, as, for example, overnight.

While not always applicable, a guiding principle which is generally advantageous is to prepare the catalyst with as large a surface area as possible.

In the catalyst preparation, relatively small amounts of other metals from the main groups of the Periodic Table or one or more of the rare earths can be added as textural promoters, i.e., to prevent undue loss of surface area of the catalyst.

The catalyst can be reactivated by burning off any carbonaceous deposit which may form after use. The burning off can be done, for example, by flushing the reactor and its contained catalyst with heated air, oxygen or air diluted with an inert gas such as nitrogen, helium or argon for a suitable time as is known in the art.

After the reactant gases have made contact with catalyst bed or series of beds, the process streams may be cooled and the products separated by known means such as distillation, crystallization, extraction by a solvent or absorption on charcoal or other media. Any portion of the starting cyclic aliphatic hydrocarbon that is not reacted may be recycled.

The oxides of group A are illustrated by aluminum oxide, cadmium oxide, cerium oxide, iron oxide, indium oxide, thorium oxide, tin oxide, titanium oxide, zinc oxide, zirconium oxide and mixtures of any two or more of them such as aluminum oxide and cadmium oxide; cerium oxide and iron oxide; indium oxide and zirconium oxide; zinc oxide, titanium oxide and aluminum oxide; zinc oxide, cerium oxide and titanium oxide; iron oxide, titanium oxide and aluminum oxide; zinc oxide, cerium oxide, titanium oxide and aluminum oxide; zinc oxide and titanium oxide; zinc oxide, titanium oxide and thorium oxide; zinc oxide, titanium oxide and zirconium oxide; and the like. Other illustrative oxides include cerium zirconate, cadmium stannate, zinc stannate, ferrous titanate, and the like.

The oxides of group B are illustrated by vanadium oxide and one or more of silver oxide, arsenic oxide, barium oxide, calcium oxide, cadmium oxide, cerium oxide, cobalt oxide, copper oxide, europium oxide, iron oxide, gagolinium oxide, hafnium oxide, indium oxide, lanthanum oxide, magnesium oxide, manganese oxide, nickel oxide, phosphorus oxide, lead oxide, antimony oxide, tin oxide, strontium oxide, titanium oxide, uranium oxide and zinc oxide. Additional illustrations include the mixtures vanadium oxide, zinc oxide and cadmium oxide; vanadium oxide, lanthanum oxide and zinc oxide; vanadium oxide, titanium oxide and aluminum oxide; vanadium oxide, magnesium oxide and zinc oxide; vanadium oxide, copper oxide and arsenic oxide; vanadium oxide, zinc oxide and cerium oxide; vanadium oxide, phosphorus oxide and zinc oxide; vanadium oxide, copper oxide and cerium oxide; vanadium oxide, nickel oxide and tin oxide; vanadium oxide, zinc oxide, titanium oxide and aluminum oxide, hafnium vanadate; europium vanadate; strontium vanadate, gadolinium vanadate; zinc metavanadate; zinc pyrovanadate; and zinc orthovanadate.

The oxides of group C are illustrated by titanium oxide and one or more of bismuth oxide, chromium oxide, copper oxide, molybdenum oxide, lead oxide, uranium oxide and tungsten oxide. Additional illustrations include titanium oxide, molybdenum oxide and bismuth oxide; and lead titanate and the like.

The oxides of group D are illustrated by zinc oxide and one or more of chromium oxide, lanthanum oxide, magnesium oxide, phosphorus oxide, silicon oxide, antimony oxide and tungsten oxide. Also illustrative are the mixtures of zinc oxide, bismuth oxide and molybdenum oxide; and zinc oxide, silicon oxide and magnesium oxide.

The oxides of group E are illustrated by aluminum oxide and one or more of copper oxide, europium oxide, lanthanum oxide, manganese oxide, lead oxide and uranium oxide.

The oxides of group F are illustrated by aluminum oxide and molybdenum oxide together, with one or more of calcium oxide, cadmium oxide, cerium oxide, copper oxide, erbium oxide, iron oxide, indium oxide, lanthanum oxide, nickel oxide, lead oxide, samarium oxide, strontium oxide, titanium oxide, uranium oxide, yttrium oxide and zinc oxide. Additional illustrations are the mixtures of aluminum oxide, molybdenum oxide, lead oxide and lanthanum oxide; aluminum oxide, molybdenum oxide, lead oxide and cerium oxide; aluminum oxide, molybdenum oxide, calcium oxide and cerium oxide; aluminum oxide, molybdenum oxide, calcium oxide and cerium oxide; aluminum oxide, molybdenum oxide, titanium oxide and cerium oxide; aluminum oxide, molybdenum oxide, cerium oxide, titanium oxide and lead oxide; aluminum oxide, molybdenum oxide, lanthanum oxide, titanium oxide and lead oxide; aluminum oxide, molybdenum oxide, cerium oxide, titanium oxide and zinc oxide; and aluminum oxide, molybdenum oxide, cerium oxide, titanium oxide and calcium oxide.

The oxides of group G are illustrated by aluminum oxide and tungsten oxide together, with one or more of calcium oxide, cerium oxide, copper oxide, iron oxide, indium oxide, lanthanum oxide, lead oxide, samarium oxide, titanium oxide, uranium oxide, and zinc oxide.

The oxides of group H are illustrated by aluminum oxide and titanium oxide together, with one or more of chromium oxide, magnesium oxide, tellurium oxide and vanadium oxide.

The oxides of group I are illustrated by aluminum oxide, titanium oxide and zinc oxide together, with one or more of silver oxide, bismuth oxide, calcium oxide, cobalt oxide, chromium oxide, copper oxide, magnesium oxide, mercury oxide, niobium oxide, nickel oxide, lead oxide, praseodymium oxide, ruthenium oxide, samarium oxide, strontium oxide, vanadium oxide, ytterbium oxide and yttrium oxide.

The oxides of group J are illustrated by aluminum oxide, molybdenum oxide and bismuth oxide together, with one or more of calcium oxide, copper oxide, lead oxide, titanium oxide and zinc oxide. Additional illustrations are the mixtures of aluminum oxide, molybdenum oxide, bismuth oxide, titanium oxide, and lead oxide; aluminum oxide, molybdenum oxide, bismuth oxide, titanium oxide and calcium oxide; and aluminum oxide, molybdenum oxide, bismuth oxide, titanium oxide and zinc oxide.

The oxides of group K are illustrated by aluminum oxide, molybdenum oxide and zirconium oxide together, with one or more of cerium oxide, titanium oxide and zinc oxide. Additional illustrations are the mixtures of aluminum oxide molybdenum oxide, zirconium oxide and cerium oxide; and aluminum oxide, molybdenum oxide, zirconium oxide, cerium oxide and titanium oxide.

The oxides of group L are illustrated by molybdenum oxide and one or more of cadmium oxide, cerium oxide, copper oxide, iron oxide, gadolinium oxide, lanthanum oxide, magnesium oxide, manganese oxide, niobium oxide, phosphorus oxide, lead oxide, titanium oxide, and zinc oxide. Also illustrative is the mixture of molybdenum oxide, lead oxide and lanthanum oxide. Further illustrations are cadmium molybdate, cerium molybdate, gadolinium molybdate, lanthanum molybdate, magnesium molybdate, manganese molybdate, lead molybdate and zinc molybdate.

The oxides of group M are illustrated by zinc oxide and titanium oxide together, with one or more of chromimum oxide, lanthanum oxide, magnesium oxide, and niobium oxide.

The oxides of Group O are illustrated by aluminum oxide and vanadium oxide together, with one or more of silver oxide, barium oxide, calcium oxide, cadmium oxide, copper oxide, gallium oxide, indium oxide, lanthanum oxide, magnesium oxide, lead oxide, strontium oxide, zinc oxide and zirconium oxide.

The oxides of group P are illustrated by zinc oxide, titanium oxide and lanthanum oxide together, with one or more of aluminum oxide, cadmium oxide, cerium oxide, thorium oxide and zirconium oxide.

SPECIFIC EMBODIMENTS OF THE INVENTION

In the following representative examples the process was continuous, carried out in the absence of air, temperatures were in degrees Centigrade, and the contact time was about 2 seconds, all unless otherwise stated.

Products of the reaction were analyzed by gas chromatography to give yields or conversions. In general, the proportions of the catalyst components are in weight percent or in molar ratios. Improved activity in the production of the aromatic amine, especially after longer times, and/or decreased amounts of less desired products such as benzonitrile, are shown to occur with the use of water.

EXAMPLE 1

Cyclohexane liquid (1.2 ml/hr) and ammonia gas (1.2 liters per hour) were passed through a ½ inch × 6 inches (1.27 × 15.24 cm) tubular reactor heated at 550° containing 3.8 g of a catalyst consisting of a 3:1 molar ratio of zinc oxide and cerium oxide impregnated into 86% titania and 14% alumina. The catalyst occupied about 3 inches (7.62 cm) of the reactor. Aniline was produced at a space-time-yield (STY) of 4.5 mg/g of catalyst/hr and the weight ratio of produced benzonitrile to aniline was 0.28.

The ammonia gas was replaced by a feed consisting of 0.6 ml of liquid 30% aqueous ammonia/hr. This corresponds to a molar ratio of 68% water calculated as mole percent of total amount of water and cyclohexane. After 21 minutes the STY was 3.4 and the ratio of benzonitrile to aniline 0.22. After an additional 21 minutes the STY was 4.9 and the ratio of a benzonitrile to aniline was 0.006.

EXAMPLE 2

The general procedure of example 1 was repeated using the same amounts of reactants with 1.1 g of a catalyst consisting of zinc oxide and vanadium oxide in the molar ratio of 1:2. Runs 1–4 were made at 550° without water, runs 5–7 with water. Table 1 gives the times of reaction, and the amounts of aniline, benzene and benzonitrile formed.

TABLE I

| Run No. | Without Water | | | | With Water | | |
|---|---|---|---|---|---|---|---|
| | 1 | 2 | 3 | 4 | 5 | 6 | 7 |
| Time (min.) | 18.5 | 18.5 | 18.7 | 19.5 | 19.5 | 20.2 | 20.3 |
| mg aniline | 1.3 | 1.0 | 0.8 | 0.8 | 1.6 | 0.7 | 0.6 |
| mg benzene | 0.9 | 0.8 | 0.9 | 2.0 | 0.8 | 2.9 | 1.8 |
| mg benzonitrile | 0.6 | 0.6 | 0.5 | 0.4 | 0.1 | 0.1 | 0.1 |

EXAMPLES 3–12

Table II summarizes results obtained from experiments with various catalysts which were charged in a tubular reactor as Example 1 and heated to 550°. Cyclohexane was introduced at 1.2 ml/hr (as liquid) and ammonia at 1.2 l/hr (as gas). In one set of experiments no water was introduced while in another water was introduced at a rate of 0.06 ml/hr (as liquid), corresponding to 26 mole percent. The results are given in (a) STY of aniline in mg/g of catalyst/hr and (b) weight ratio of benzonitrile to aniline formed. The oxides used in the catalysts of Table II are in molar proportions except as indicated otherwise. In all instances the amount of byproduct benzonitrile was reduced when water was used. In Examples 4 and 7–13, moreover, the amount of aniline was increased when water was used.

Table II

| Example | Catalyst | | STY Aniline | | Benzonitrile/ Aniline | |
|---|---|---|---|---|---|---|
| | | | Without Water | With Water | Without Water | With Water |
| 3 | Ti 0.431 Zn 0.0185 Al 0.00637 Cr 0.00125 | oxides | .96 | 3.6 | .36 | .07 |
| 4(1) | Al 0.147 Zr 0.021 Ce 0.00448 | oxides | .44 | 1.2 | .34 | .07 |
| 5 | 3Ti/Cr | oxides | .89 | 1.0 | .29 | .01 |
| 6(2) | ZnS/9 Al$_2$O$_3$ | | .31 | .55 | .34 | .29 |
| 7 | 4 Ti/Zn/La | oxides | .05 | .38 | 14.00 | 3.80 |
| 8 | ZnMoO$_4$ | | .42 | .32 | .16 | .07 |
| 9(2) | 1.6 La$_2$O$_3$ MoO$_3$ 9 Al$_2$O$_3$ | | .08 | .27 | 1.40 | .56 |
| 10(2) | Uranium Oxide/ 9 Al$_2$O$_3$ | | .43 | .27 | .50 | .24 |
| 11 | V$_2$O$_5$/TiO$_2$/Al$_2$O$_3$ | | .27 | .16 | .83 | .40 |
| 12 | ZnO/2 Bi$_2$O$_3$/3 MoO$_3$ on SiO$_2$ (50/50) | | .03 | .14 | 1.00 | 0.0 |
| 13 | Al 0.39 Pb 0.02 | oxides | .04 | .11 | .87 | .78 |

Table II-continued

| | | STY Aniline | | Benzonitrile/ Aniline | |
|---|---|---|---|---|---|
| Example | Catalyst | Without Water | With Water | Without Water | With Water |
| | W 0.02 | | | | |

(1)reaction temperature of 500° C.
(2)weight ratio in catalyst

EXAMPLE 14

A quartz reaction tube approximately 18 inches in length and 1 inch diameter was charged in its midsection with 10 cc in volume (10.95g) of a catalyst consisting of 10% ZnO and 90% of 86 $TiO_2$/14 $Al_2O_3$. The catalyst bed was heated to 500° and ammonia gas (4.4 l/hr) and cyclohexane (3.79 g/hr) passed through the reactor. No water was present. The effluent gas was sampled at various times by gas chromatography. The yields of aniline and ratios of less desired benzene and benzonitrile to aniline at various time intervals are shown in Table III.

Table III

| | (Without Water) | | |
|---|---|---|---|
| Time (min) | 10 | 184 | 394 |
| Yield of aniline (mg/hr/g catalyst) | 10.95 | 3.84 | 1.97 |
| Benzene/aniline | .78 | 3.87 | 8.67 |
| Benzonitrile/aniline | .01 | .22 | .34 |

The above was repeated except that water (0.09 g/hr corresponding to 10 mole percent) was added to the flow of reactants. The beneficial effect on catalyst lifetime, and decreased ratio of undesirable products is demonstrated in Table IV.

Table IV

| | (With Water) | | |
|---|---|---|---|
| Time (min) | 14 | 194 | 379 |
| Yield of aniline (mg/hr/g catalyst) | 10.6 | 8.6 | 7.2 |
| Benzene/aniline | .64 | 1.23 | 1.76 |
| Benzonitrile/aniline | 0 | 0 | .02 |

EXAMPLES 15-19

The following examples were all run with the same charge of catalyst, 10 cc in volume (6.51 g) of ZnO/CeO$_2$/TiO$_2$, under the same conditions of Example 14. The only variable in each run was the amount of water added to the reactant stream. In Table V, which gives the results after 1 hour of operation, the amount of water is given as mole percent of the cyclohexane and water combined. In each instance using water the amount of aniline was increased and the amount of benzene and benzonitrile was reduced.

TABLE V

| | Example | | | | | |
|---|---|---|---|---|---|---|
| | Control | 15 | 16 | 17 | 18 | 19 |
| Mole % H$_2$O | 0 | 1 | 3.3 | 10 | 12.7 | 32 |
| Yield of aniline (mg/hr/g catalyst) | 10.5 | 10.7 | 21.1 | 32.1 | 29.9 | 28.8 |
| Benzene/aniline | 2.68 | 2.16 | 1.28 | 1.16 | .83 | .64 |
| Benzonitrile/aniline | .21 | .19 | .05 | .04 | 0 | 0 |

EXAMPLES 20-22

A. The catalyst in each of these examples was charged in a tubular reactor and heated to 500° C. A reactant flow of 0.13 moles/hour ammonia and 0.067 moles/hour cyclohexane were passed over the catalyst. Analysis of the reactor effluent after 30 minutes showed the relative proportion of aniline and benzonitrile produced.

B. In a second set of experiments the conditions and reactant flow were as above but with the addition of 0.04 moles/hour water. Analysis of the reactor effluent was also made after 30 minutes.

The results in Table VI show that the presence of water enhances the production of aniline and decreases Table VI

| Ex. | Catalyst as Oxides Mol. Proportion | | Amount of Catalyst - Gm | Mol Percent Aniline | | Mol Percent Benzonitrile | |
|---|---|---|---|---|---|---|---|
| | | | | Without Water | With Water | Without Water | With Water |
| 20 | Al | 10.0 | | | | | |
| | Mo | 0.7 | 3.9 | 0.134 | 0.27 | 0.057 | 0.002 |
| | Bi | 0.1 | | | | | |
| | Zn | 1.0 | | | | | |
| 21 | Al | 10.0 | | | | | |
| | Mo | 0.7 | 4.1 | 0.108 | 0.28 | 0.043 | 0.005 |
| | Zr | 0.1 | | | | | |
| | Zn | 1.0 | | | | | |
| 22 | Al | 1.0 | | | | | |
| | V | 0.2 | 1.7 | 0.668 | 0.35 | 0.045 | 0.000 |
| | Zn | 0.1 | | | | | | that of benzonitrile. Example 22, for instance, shows the production of unwanted benzonitrile was completely eliminated while aniline was still being produced.

EXAMPLE 23

Hydrate cerium nitrate was calcined at 250° C. for 2 hours and then at 500° C. for 5 hours. The resultant cerium oxide was ground and 4 g of it were placed approximately in the middle of a ½ inch × 6 inch tubular reactor. The reactor and its contained catalyst were heated to 575° C. while nitrogen gas was passed through. After all absorbed water on the catalyst had been evaporated cyclohexane at a rate of 2 ml per hour and ammonia gas at a rate of 21 ml per minute were passed over the heated catalyst in the tube for 60 minutes. The liquid effluent was collected between 45 and 60 minutes.

In a second run the above experiment was repeated with a fresh batch of the same catalyst and in addition water at the rate of 0.25 ml per hour was added to the feed. The effluent was collected as above.

The effluent liquids in each instance were analyzed by GC using a dual column system at 180°, a first column of 5 feet × 1/8 inch Carbowax ® 20 M and a second column of UCW-98 (silicone polymer containing methyl and vinyl groups, dispersed on chromosorb W). Aniline with a retention time of 11.4 minutes was detected in both runs. Benzonitrile with a retention time of 8.3 minutes was detected in the run when no water was used; it was not detectable in the run when water was used.

EXAMPLE 24

Ten ml (6.51 g) of 8-14 mesh fraction of a Ti—Zn—Th oxide catalyst (as described below) was charged into a 1 inch O.D. tubular quartz reactor and heated to 500° C. A reactant flow of 0.13 moles/hr ammonia, 0.094 moles/hr cyclohexane and 0.014 moles/hr water was passed over the catalyst. Analysis of the reactor effluent after 15 minutes showed a 4.0% conversion to aniline, 18% conversion to benzene and 1.1% conversion to cyclohexene. No benzonitrile could be detected in the product.

The catalyst employed above was prepared as follows:

An aqueous solution of Ti(IV) was prepared by addition of 104 g of $TiCl_4$ to 250 g of ice. After dilution with 1500 ml of water, 18.15 g of $Zn(NO_3)_2.6H_2O$ and 1.77 g of $ThCl_4$ were added. The resulting solution was stirred and heated to 75°–80° C and concentrated aqueous ammonia was added dropwise to a pH of 7.0. After 30 minutes, the precipitate was collected by filtration and washed repeatedly until the filtrate was free of chloride ion as determined by test with aqueous silver nitrate solution. The filter cake was dried at 120° and then calcined for 30 minutes each at 200°, 300° and 400° and finally for 15.5 hrs at 520°–525° C.

EXAMPLE 25

A. A catalyst was prepared by thoroughly mixing together

| Compound | Grams |
| --- | --- |
| $Al(NO_3)_3 . xH_2O$ | 17.4 |
| $CdNO_3 . xH_2O$ | 4.8 |
| $Ce(NO_3)_3 . xH_2O$ | 5.3 |
| $Fe(NO_3)_3 . xH_2O$ | 11.5 |
| $In_2O_3$ | 2.8 |
| $SnO_2$ | 3.0 |
| $ThO_2$ | 2.0 |
| $TiO_2$ | 2.0 |
| $Zn(NO_3)_2 . xH_2O$ | 7.3 |
| $ZrO(NO_3)_2 . xH_2O$ | 4.4 |
| Water | 150.0 |

The resultant slurry-solution was evaporated to dryness on a hot plate. The solids were calcined for a total of 7 hours at the following temperatures and in the sequence shown:

| ° C | Hours |
| --- | --- |
| 200 | 1 |
| 300 | 1 |
| 400 | 1 |
| 500 | 4 |

The catalyst was then ground to 10-20 mesh.

B. Aniline was made from cyclohexane using the above catalyst as follows. A three inch section of a Vycor ® tubular reactor having a 0.5 inch inside diameter was loaded with 5 g of the catalyst. Anhydrous ammonia was then passed through the reactor while the temperature of the reactor and its contained catalyst was raised to 525° C. When all the water adsorbed on the catalyst had been evaporated off, the ammonia flow was adjusted to a rate of 21 ml per minute and a flow of cyclohexane at 2 ml per hour was started. The effluent was collected in a zero degree cold trap for 30 minutes and the collected liquid analyzed by GC using a dual column system of 5 inch × ⅛ inch Carbowax ® 20 M and 5 inch × ⅛ inch UCW-98 (silicone polymer containing methyl and vinyl groups) dispersed on Chromsorb W at 180° C. Aniline with a retention time of 11.4 minutes was detected and the amount produced was 1.9% of the collected liquid.

C. The procedure of part B was followed except that 0.25 ml water per hour was added to the feed. After a 30 minute run the analysis for aniline was performed using the same GC column but with a different temperature program. The initial temperature of 80° was held for 4 minutes and then raised to 210°. Aniline with a retention time of 10.8 minutes was detected and the amount produced was 2.2%.

EXAMPLE 26

A. Catalyst 7.4 ZnO/1.2 $La_2O_3$/91.4 $TiO_2$ (wt%)

A solution was prepared by adding 105.3 g of $TiCl_4$ to 500 g ice. This was diluted with 2 liters of water and 18.56 g $ZnNO_3.6H_2O$, 1.51 g lanthanum nitrate hexahydrate and 106.1 g of urea were added. The resulting mixture was stirred and heated to reflux for 15-16 hours. The precipitate which formed was collected by filtration and washed repeatedly with hot distilled water to remove chloride ion. A sample of the supernatant liquid was analyzed for zinc. It contained 475 parts per million indicating incomplete precipitation of all the zinc. The precipitated material was dried at 120°, crushed, sieved and calcined at 530° for 15.5 hours. Based on the recovered zinc in the supernatant fluid, the catalyst comprised 7.4 wt% zinc oxide, 1.2 wt% lanthanum oxide and 91.4 wt% titanium dioxide.

B. Preparation of Aniline at 500°

A sample of 14.39 g of 8-14 mesh zinc oxide/lanthanum oxide/titanium oxide catalyst prepared above was loaded into a tubular reactor mounted in a split tube resistance furnace. Reactants were fed to the reactor via conventional pumps and gas manifolds. The effluent from the reactor passed directly to the gas sampling loop of a gas chromatograph. The catalyst was heated to 500° C and ammonia (0.46 mole/hr), cyclohexane (0.31 mole/hr) and water (0.10 mole/hr) were passed over the catalyst. Analysis of the effluent from the reactor at the end of 15 minutes showed that aniline was being formed at the rate of 0.059 g per g of catalyst per hour. At the end of one hour aniline was being formed at the rate of 0.051 g per g of catalyst per hour. The ratio of benzene formed to aniline formed was 0.05-0.6 and there was no benzonitrile formed.

EXAMPLE 27

The catalyst in Example 26 was regenerated by passing a mixture of helium and air over the catalyst in the reactor at 500° until all coke deposits had been removed. The air and helium flow was discontinued and the catalyst temperature increased to 520° C. Ammonia (0.945 mole/hr), cyclohexane (0.63 mole/hr) and water (0.126 mole/hr) were passed over the catalyst. At the end of 15 minutes the effluent was analyzed by gas chromatography. Aniline was being produced at the rate of 0.128 g/g catalyst/hr. The ratio of benzene/aniline was 0.73 and there was no benzonitrile formed.

EXAMPLE 28

A. Catalyst 4.71 ZnO/2.85 $ZrO_2$/92.44 $TiO_2$ (wt%)

A solution prepared by adding 109.7 g of titanium tetrachloride to 500 g of ice was diluted with 2 liters of water. To the resulting solution was added 8.61 g of zinc nitrate hexahydrate and 3.73 g of zirconium oxychloride octahydrate. The solution was stirred vigorously and heated to reflux, as concentrated ammonium hydroxide was added to a pH of 7.0. The reflux was continued for one hour and a small additional amount of ammonium hydroxide was added to readjust the pH to 7. The precipitate was collected by filtration and washed repeatedly with distilled water to remove chloride ion. Finally the catalyst was dried at 120° C, crushed, sieved and calcined in air for 15.5 hrs at 530° C.

B. Synthesis of Aniline

A sample of 8.77 g of 8–14 mesh catalyst as prepared above was charged into a tubular quartz reactor as described in Example 26. The catalyst was heated to 500° and ammonia (0.242 mole/hr), cyclohexane (0.16 mole/hr) and water (0.05 mole/hr) passed through the reactor. The effluent was analyzed by gas chromatography at the end of 15 minutes. Aniline was being formed at the rate of 0.076 g/g catalyst/hr. The ratio of benzene/aniline was 0.42 and there was no benzonitrile produced.

EXAMPLE 29

A. Catalyst 4.38ZnO/1.58 $ThO_2$/94.03 $TiO_2$ (wt%)

A solution was prepared by addition of 111.6 g of titanium tetrachloride to 500 g of ice. This was diluted with 2 liters of water and 7.99 g of zinc nitrate hexahydrate, 1.66 g of thorium nitrate tetrahydrate and 90.8 g of urea added. The resulting reaction mixture was stirred and heated to reflux for 15–16 hours. The precipitate was collected by filtration and washed repeatedly with hot, distilled water to remove chloride ion. Finally the catalyst was dried at 120° C, crushed, sieved and calcined for 15.5 hours at 530° C.

B. Synthesis of Aniline

The procedure of Example 26 was repeated except that the reactor was charged with 6.90 g of ZnO/$ThO_2$/$TiO_2$ prepared as above. The same flows of ammonia, cyclohexane and water were used as in Example 28. At the end of 15 minutes aniline was being produced at the rate of 0.070 g/g catalyst/hr. The ratio of benzene/aniline formed was 0.28 and no benzonitrile was formed.

EXAMPLE 30

A. Catalyst 95 $TiO_2$/2.4 ZnO/0.92 $ZrO_2$/1.2 $La_2O_3$(wt%)

484.85 g of an aqueous solution containing 0.0015 moles of $TiCl_4$ per g of solution, 5.41 g $ZnNO_3.6H_2O$, 1.88 g $ZrONO_3.nH_2O$, and 2 g $La(NO_3)_3.6H_2O$, were thoroughly mixed in 3 liters water and heated to reflux. Concentrated $NH_4OH$ was added to pH 5.8. The precipitate which formed was filtered off and washed four times with 3 liter portions of water. The concentration of chloride ion in the last water wash was 12 ppm. The washed precipitate was dried at 125° C. and then calcined at 525° C. for 3 hours.

B. Preparation of Aniline 7.2 g of the catalyst as prepared above was charged into a tubular reactor as in Example 26. The reactor containing the catalyst was heated to 500° and ammonia (0.342 mole/hr), cyclohexane (0.228 mol/hr) and water (0.076 mol/hr) were passed through. The effluent was analyzed by gas chromatography after various times had elapsed, with the following results in g of aniline/g catalyst/hr:

|  | 15 min. | 60 min. | 80 min. |
|---|---|---|---|
| Aniline | 0.046 | 0.043 | 0.050 |

The ratio of benzene/aniline was 0.9 and again no benzonitrile was formed.

EXAMPLE 31

The effect of reactivating the catalyst is shown in this example.

A. Catalyst 89% $TiO_2$/9.8% ZnO/1.2% $La_2O_3$ (Wt.%)

An aqueous solution (474.3g) containing 0.696 moles $TiCl_4$, 2.0 g $La(NO_3)_3.6H_2O$, 22.4 g $Zn(NO_3)_2.6H_2O$ and 127.5 g urea were mixed in a 5 liter flask with 1500 ml distilled, deionized water and quickly heated to reflux with agitation. After 16 hrs. the precipitate was filtered off and washed five times with distilled, deionized water. The final wash contained about 80 ppm $Cl^-$. After drying 16 hrs in an air circulating oven at 120° to 130° C and calcining at 525° for 4 hrs the catalyst had a nitrogen surface area of 99.9 $m^2/g$.

B. Preparation of Aniline

The procedure of Example 26 was repeated with 15 g of the the catalyst of part A above. The feeds were:

| cyclohexane | 0.0131 mol/min. |
|---|---|
| water | 0.0021 mol/min. |
| ammonia | 0.026 mol/min. |

The run was started at 550° C in the catalyst bed but lowered to 530° as soon as the feed mixture contacted the bed. The reactor effluent was analyzed periodically by gas chromatography. Space time yield (g aniline/g catalyst hr.) vs. time elapsed are shown in Table VII.

C. After 3.65 hrs of running the reaction of part B above, the feeds were stopped and the reactor purged with nitrogen at 390 ml.min. After about 30 minutes of purging, air was started at 170 ml/min and continued until all the carbon or coke had been removed from the catalyst by oxidation to CO and $CO_2$ (about 35 min). The air was stopped and the excess left in the reactor was removed by nitrogen. The nitrogen stream was stopped and the reaction restarted using the conditions of part B above. The space time yields of aniline are given in Table VII.

TABLE VII

| Initial Reaction (Part B) | | Reaction After Reactivation of Catalyst (Part C) | |
|---|---|---|---|
| Time hours | STY Aniline | Time hours | STY Aniline |
| 0.2 | 0.146 | 0.9 | 0.13 |
| 0.7 | 0.110 | 1.2 | 0.09 |
| 1.2 | 0.095 | 1.8 | 0.065 |
| 1.7 | 0.065 | 2.25 | 0.052 |
| 2.2 | 0.055 | 2.7 | 0.045 |
| 2.7 | 0.045 | 3.2 | 0.035 |

TABLE VII-continued

| | Initial Reaction (Part B) | Reaction After Reactivation of Catalyst (Part C) | |
|---|---|---|---|
| Time hours | STY Aniline | Time hours | STY Aniline |
| 3.2 | 0.035 | | |
| 3.65 | 0.030 | | |

EXAMPLE 32

Catalyst 88.8% $TiO_2$/10.1% ZnO/0.6% $La_2O_3$/1.2% $CeO_2$ (mol. %)

A solution was prepared by addition of 100.9 g $TiCl_4$ to 500 g of ice followed by dilution with 1500 ml of water. To this was added 18.15 g of $Zn(NO_3)_2 \cdot 6H_2O$, 3.15 g of $Ce(NO_3)_3 \cdot 6H_2O$ and 3.32 g (0.00744 mole) of $La(NO_3)_3 \cdot 6H_2O$. The solution was stirred and heated to 75°-80° C and concentrated aqueous $NH_3$ added to pH 7.0. The slurry was stirred for 30 minutes and filtered. The solid was washed repeatedly until free of chloride ion as determined by test of the wash water with silver nitrate solution. The filter cake was dried at 120° C and then crushed and sieved. The catalyst was calcined for 13.5 hrs at 515° C. The surface area was 123 $m^2$/g.

A 7.38 g portion of 8-14 mesh granules of this catalyst were charged to a quartz reactor and heated to 500° C. Cyclohexane (4.50 × $10^{-2}$ mole/hr), ammonia (1.8 × $10^{-1}$ mole/hr.) and water (6.1 × $10^{-3}$ mole/hr.) were passed over the catalyst. At the end of one hr aniline was being formed at the rate of 0.024 g/g catalyst/hr. The conversion to aniline was 4.2% and the ratio of benzene formed to aniline was 0.8.

EXAMPLE 33

Catalysts 97.3% $TiO_2$/2.4% ZnO/0.3% $CeO_2$ (mol. %)

A solution containing 3 moles $TiCl_4$, 0.075 moles zinc nitrate, 0.0094 moles of cerium nitrate and 9.1 moles urea were mixed 16 liters of distilled, deionized water. The solution was heated to reflux and neutralized with concentrated ammonium hydroxide to pH 7.0. After 1 hr the pH was readjusted to pH 7.0 and the precipitate filtered, washed 5 times with fresh distilled, deionized water, dried at 120° C and calcined at 525° C for 3 hours.

A charge of 7.43 g (8-14 mesh granules) of the above catalyst was placed in a 1 inch O.D. quartz reactor and heated to 500° C. Ammonia (0.0056 moles/min.) cyclohexane (0.0037 moles/min.) and water (0.0011 moles/min.) were introduced into the top of the reactor. The reactor effluent was collected at the bottom in a trap of 0° C and the products analyzed by gas chromatography. The results are shown below.

| Sample | Elasped Time (minutes) | g Aniline/g cat./hr. |
|---|---|---|
| 1 | 15 | 0.033 |
| 2 | 30 | 0.033 |
| 3 | 60 | 0.033 |
| 4 | 90 | 0.033 |
| 5 | 120 | 0.032 |

EXAMPLE 34

This example illustrates the effect of air on the reaction. A quartz flow reactor was charged with 7.56 g of 8-14 mesh 15% zinc oxide on titania. The catalyst was pretreated with a mixture of air at 500° C for 30 min. The air was stopped and a mixture of cyclohexane (3.79 g/hr.) ammonia (73.4 ml./min) and water (0.11 g/hr.) was passed through the reactor for 1.5 hours. Effluent from the reactor was collected in cooled traps for three successive 30 minute intervals. Liquid samples were analyzed by gas chromatography.

The catalyst was regenerated at 500° with air, and the reaction started again. The flows of cyclohexane and water were the same as above. The flow of ammonia was 55 ml./min. and air (18.4 ml./min.) was added to the reactant flow. The oxygen to cyclohexane molar ratio was about 0.2 to 1. The reaction was continued for 1.5 hours and effluent collected for three successive 30 minute periods as above and analyzed as above.

The products from the reaction run in the presence of air contained more by-products than those run in the absence of air. Many of these were unidentified, and only approximate calculation of yields and conversions could be made. There was little difference in the conversions to aniline. Comparisons of the runs follow:

| Sample collected at time interval | Without Air | | | With Air | | |
|---|---|---|---|---|---|---|
| | 1 | 2 | 3 | 4 | 5 | 6 |
| Cyclohexane Conversion (%) | 5.9 | 4.2 | 4.8 | 12.6 | 13.6 | 12.2 |
| Conversion to Aniline (%) | 2.8 | 2.1 | 2.6 | 2.5 | 2.8 | 3.0 |
| Conversion to Benzene (%) | 1.8 | 0.9 | 1.0 | 7.5 | 7.3 | 6.0 |

EXAMPLE 35

A. Catalyst 2.87 ZnO/2.60 $V_2O_5$/4.98 $CeO_2$/89.55 $TiO_2$ (wt%)

To 427 g of an aqueous solution containing 0.30 g $TiCl_4$ per gram, there was added 2.91 g ammonium vanadate, 7.57 g cerium nitrate hexahydrate, 6.14 g zinc nitrate hexahydrate and 2500 ml water. This solution was heated to reflux with stirring and concentrated ammonium hydroxide solution was added to pH 7.0. After one hour of continued refluxing the pH was again adjusted to 7.0 with ammonium hydroxide and the precipitated catalyst collected by filtration. The precipitated material was washed repeatedly with hot distilled water until the chloride ion concentration in the filtrate was less than 10 ppm. The catalyst was dried at 120° and then calcined at 525° for 3 hours following which it was crushed and sieved to 14-20 mesh.

B. Preparation of Aniline

A stainless steel tubular reactor approximately ½ inch in diameter was charged with 10 ml (6.81 g) of the catalyst of part A. A flow of anhydrous ammonia (2.09 × $10^{-2}$ moles per minute), cyclohexane (0.833 moles per hour) and water (0.25 mole per hour) was passed over the catalyst at 525° and 100 psig. Liquid products were condensed and analyzed by gas chromatography. During a two hour run aniline was formed at an average STY of 0.218 g/g catalyst/hour.

EXAMPLE 36

A. Catalyst 2.77 ZnO/5.20 $V_2O_5$/4.94 $La_2O_3$/87.08 $TiO_2$ (wt%)

This catalyst was produced using 419 g of an aqueous solution containing 0.299 g $TiCl_4$ per gram of solution to which there was added 6.14 g zinc nitrate hexahydrate, 4.06 g ammonium vanadate and 7.96 g lanthanum nitrate hexahydrate and 2500 ml water. This solution was then heated, etc., as in Example 35 A.

B. Preparation of Aniline 7.75 Grams of the above catalyst were placed in a tubular reactor and the same flow rates and conditions of Example 35 B were used. After a two hour run the major product was aniline which formed at the rate of 0.198 g/0.198 g/g catalyst/hour.

I claim:

1. The process which consists in heating a cyclic aliphatic hydrocarbon of the formula

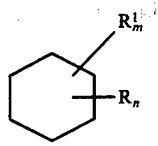

with ammonia at 300°–650° C. to produce a compound of the formula

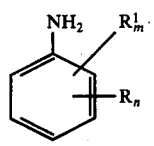

wherein
R and $R^1$ individually are alkyl of 1–4 carbon atoms and
m and n individually are 0 or 1,
where the heating is carried out in the presence of about 1 to 70 mole percent of water based on the total amount of water and the said cyclic aliphatic hydrocarbon, at a contact time of about 0.1 second to about 10 minutes, and in the presence of a catalyst selected from:

A. one or more oxides of Al, Cd, Ce, Fe, In, Sn, Ti, Th, Zn and Zr;
B. vanadium oxide and one or more oxides of Ag, As, Ba, Ca, Cd, Ce, Co, Cu, Eu, Fe, Gd, Hf, In, La, Mg, Mn Ni, P, Pb, Sb, Sn, Sr, Ti, U and Zn;
C. titanium oxide and one or more oxides of Bi, Cr, Cu, Mo, Pb, U and W;
D. zinc oxide and one or more oxides of Cr, La, Mg, P, Si, Sb, W and the pair of Bi and Mo;
E. aluminum oxide and one or more oxides of Cu, Eu, La, Mn, Pb and U;
F. aluminum oxide, molybdenum oxide and one or more oxides of Ca, Cd, Ce, Cu, Er, Fe, In, La, Ni, Pb, Sm, Sr, Ti, U, Y and Zn;
G. aluminum oxide, tungsten oxide and one or more oxides of Ca, Ce, Cu, Fe, In, La, Pb, Sm, Ti, U and Zn;
H. aluminum oxide, titanium oxide and one or more oxides of Cr, Mg, Te and V;
I. aluminum oxide, titanium oxide, zinc oxide and one or more oxides of Ag, Bi, Ca, Co, Cr, Cu, Hg, Mg, Nb, Ni, Pb, Pr, Ru, Sm, Sr, V, Yb and Y;
J. aluminum oxide, molybdenum oxide, bismuth oxide and one or more oxides of Ca, Cu, Pb, Ti and Zn;
K. aluminum oxide, molybdenum oxide, zirconium oxide and one or more oxides of Ce, Ti and Zn;
L. molybdenum oxide and one or more oxides of Cd, Ce, Cu, Fe, Gd, La, Mg, Mn, Nb, P, Pb, Ti and Zn;
M. zinc oxide, titanium oxide and one or more oxides of Cr, La, Mg and Nb; and
N. CdS; CoS; CdS/aluminum oxide; CdS/titanium oxide/aluminum oxide; chromium sulfide; ZnSe; ZnS; ZnTe; ZnS/aluminum oxide; CdS/ZnS/aluminum oxide; and $WS_2$;
O. Aluminum oxide, vanadium oxide and one or more oxides of Ag, Ba, Ca, Cd, Cu, Ga, In, La, Mg, Pb, Sr, Y, Zn and Zr; and
P. Zinc oxide, titanium oxide, lanthanum oxide and one or more oxides of Al, Cd, Ce, Th and Zr.

2. The process of claim 1 carried out in a nonoxidative atmosphere.
3. The process of claim 1 in which the water is present in the range of about 3 to about 32 mole percent.
4. The process of claim 1 in which the temperature range is 450°–550° C.
5. The process of claim 1 in which the molar ratio of the cyclic alphatic hydrocarbon to ammonia ranges from 5/1 to 1/10.
6. The process of claim 1 in which the cyclic aliphatic hyrdrocarbon is cyclohexane.
7. The process of claim 1 in which the contact time is about 1 second to about 8 minutes.
8. The process of claim 1 in which the catalyst is selected from group A.
9. The process of claim 1 in which the catalyst is selected from group B.
10. The process of claim 1 in which the catalyst is selected from Group C.
11. The process of claim 1 in which the catalyst is selected from Group D.
12. The process of claim 1 in which the catalyst is selected from Group E.
13. The process of claim 1 in which the catalyst is selected from Group F.
14. The process of claim 1 in which the catalyst is selected from Group G.
15. The process of claim 1 in which the catalyst is selected from Group H.
16. The process of claim 1 in which the catalyst is selected from Group I.
17. The process of claim 1 in which the catalyst is selected from Group J.
18. The process of claim 1 in which the catalyst is selected from Group K.
19. The process of claim 1 in which the catalyst is selected from Group L.
20. The process of claim 1 in which the catalyst is selected from Group M.
21. The process of claim 1 in which the catalyst is selected from Group N.
22. The process of claim 1 in which the catalyst is selected from Group O.
23. The process of claim 1 in which the catalyst is selected from Group P.
24. The process of claim 1 in which a member of Group A or vanadium oxide comprises half or more of a multicomponent catalyst.
25. The process of claim 1 in which the catalyst contains zinc oxide and titanium oxide.
26. The process of claim 1 in which the catalyst contains zinc oxide and vanadium oxide.
27. The process of claim 1 in which the catalyst contains zinc oxide, vanadium oxide, cerium oxide and titanium oxide.
28. The process of claim 1 in which the catalyst contains zinc oxide, vanadium oxide, lanthanum oxide and titanium oxide.
29. The process of claim 1 in which the catalyst contains zinc oxide, titanium oxide and lanthanum oxide.

30. The process of claim 1 in which the catalyst contains zinc oxide, titanium oxide and thorium oxide.

31. The process of claim 1 in which the catalyst contains zinc oxide, titanium oxide and zirconium oxide.

32. The process of claim 1 in which the catalyst contains zinc oxide, titanium oxide, zirconium oxide and lanthanum oxide.

33. The process of claim 1 in which the catalyst contains aluminum oxide, titanium oxide, zinc oxide and cerium oxide.

34. The process of claim 1 in which the catalyst contains vanadium oxide, cadmium oxide and zinc oxide.

35. The process of claim 1 in which the catalyst contains aluminum oxide, zirconium oxide and cerium oxide.

36. The process of claim 1 in which the catalyst contains aluminum oxide, titanium oxide, zinc oxide and cadmium oxide.

* * * * *